(12) United States Patent
Madan et al.

(10) Patent No.: US 9,750,711 B2
(45) Date of Patent: Sep. 5, 2017

(54) LOW DOSE ORAL PHARMACEUTICAL COMPOSITION OF ISOTRETINOIN

(71) Applicant: Sun Pharmaceutical Industries Limited, Mumbai, Maharashtra (IN)

(72) Inventors: Harish Kumar Madan, Haryana (IN); Rathinasabapathy Venkateshwaran, Tamil Nadu (IN); Sumit Madan, Delhi (IN); Ravi Kochhar, Haryana (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/444,571

(22) Filed: Feb. 28, 2017

(65) Prior Publication Data

US 2017/0165218 A1 Jun. 15, 2017

Related U.S. Application Data

(63) Continuation-in-part of application No. 14/958,467, filed on Dec. 3, 2015, which is a continuation of application No. PCT/IB2015/054080, filed on May 29, 2015.

(30) Foreign Application Priority Data

Oct. 1, 2014 (IN) ............................ 2827/DEL/2014

(51) Int. Cl.

| | |
|---|---|
| A61K 31/202 | (2006.01) |
| A61K 47/02 | (2006.01) |
| A61K 9/48 | (2006.01) |
| A61K 47/22 | (2006.01) |
| A61K 47/12 | (2006.01) |
| A61K 47/32 | (2006.01) |
| A61K 9/00 | (2006.01) |
| A61K 47/14 | (2017.01) |
| A61K 31/203 | (2006.01) |
| A61K 47/24 | (2006.01) |
| A61K 47/10 | (2017.01) |

(52) U.S. Cl.
CPC .......... *A61K 31/203* (2013.01); *A61K 9/0053* (2013.01); *A61K 9/4858* (2013.01)

(58) Field of Classification Search
CPC .... A61K 9/4858; A61K 31/203; A61K 47/10; A61K 47/44; A61K 9/0014; A61K 9/1075; A61K 9/4866; A61K 31/202; A61K 47/14; A61K 31/57; A61K 31/7048; A61K 38/13; A61K 9/1617; A61K 9/4808; A61K 9/4875; A61K 9/5015; A61K 9/5026

See application file for complete search history.

(56) References Cited

U.S. PATENT DOCUMENTS

| | | | |
|---|---|---|---|
| 7,435,427 B2 | 10/2008 | Vanderbist et al. | 424/439 |
| 8,367,102 B2 | 2/2013 | Vanderbist et al. | 424/451 |
| 2003/0077297 A1 | 4/2003 | Chen et al. | 424/400 |
| 2005/0129773 A1 | 6/2005 | Bhatia et al. | 424/489 |
| 2014/0107203 A1* | 4/2014 | Deboeck | A61K 9/4875 514/559 |

FOREIGN PATENT DOCUMENTS

| | | | | |
|---|---|---|---|---|
| IN | WO2010/134047 A2 * | 11/2010 | | A61K 9/00 |
| WO | WO00/25772 | * 10/1999 | | A61K 31/203 |
| WO | WO 2012/053013 | 4/2012 | | A61K 9/107 |

OTHER PUBLICATIONS

Layton, Alison. "The use of isotretinoin in acne", Dermato-Endocrinology 1:3, 162-169; May/Jun. 2009.*
Co-pending PCT Application No. PCT/IB2015/054080, filed on May 29, 2015, published as WO 2016/051288 on Apr. 7, 2016.
International Search Report and Written Opinion for International Application No. PCT/IB2015/054080, issued by US/ISA dated Oct. 6, 2015.
International Preliminary Report on Patentability for International Application No. PCT/IB2015/054080, issued by WIPO dated Apr. 13, 2017.
Office Action for U.S. Appl. No. 14/958,467, issued by USPTO dated Apr. 20, 2016.
Final Office Action for U.S. Appl. No. 14/958,467, issued by USPTO dated Oct. 17, 2016.
Office Action for U.S. Appl. No. 14/958,467, issued by USPTO dated May 19, 2017.
Co-pending U.S. Appl. No. 14/958,467, filed Dec. 3, 2015, published as US 2016/0128962 on May 12, 2016.

* cited by examiner

*Primary Examiner* — Audrea Buckley

(57) ABSTRACT

The present invention provides a low dose oral pharmaceutical composition of isotretinoin having reduced food effect, in particular no food effect. The present invention further relates to a process for preparing the oral pharmaceutical composition of the present invention.

9 Claims, No Drawings

LOW DOSE ORAL PHARMACEUTICAL COMPOSITION OF ISOTRETINOIN

FIELD OF THE INVENTION

The present invention provides a low dose oral pharmaceutical composition of isotretinoin having reduced food effect, in particular no food effect. The present invention further relates to a process for preparing the oral pharmaceutical composition of the present invention.

BACKGROUND OF THE INVENTION

Isotretinoin is a retinoid (also known as 13-cis retinoic acid). Owing to its low water solubility, the oral bioavailability of isotretinoin is low. PCT Publication No. WO 00/25772 discloses that the presently marketed formulation of isotretinoin, i.e., Accutane®, contains isotretinoin at a mean particle size of about 100 μm resulting in only 20% oral bioavailability.

U.S. Pat. Nos. 7,435,427 and 8,367,102 cover the marketed formulation of Absorica®. These patents disclose capsules comprising a semi-solid suspension of isotretinoin containing at least two lipidic excipients, one having an HLB value equal to or greater than 10 and the other being an oily vehicle. These patents are based on the use of the "Lidose® technology" to provide a formulation of isotretinoin with enhanced bioavailability.

Isotretinoin has a very high teratogenic potential. This drug may be prescribed only by or under the supervision of a consultant dermatologist. Therefore, reduction of dose in case of such a teratogenic drug is highly beneficial. Further, isotretinoin is known to have a "food effect", i.e., its absorption is dependent on the presence of food in the stomach. Therefore, there is a need to develop a composition of isotretinoin which has a lower dose and reduced food effect. The present inventors have developed an oral pharmaceutical composition of isotretinoin, wherein said composition has enhanced bioavailability, lower dose and reduced food affect, in particular no food effect in comparison to the marketed formulations of isotretinoin, e.g. Roaccutane® and Absorica®. These advantages would lead to better patient compliance.

Further, the present inventors were able to develop an isotretinoin composition having low isotretinoin to excipient ratio which would allow for it to be filled in a capsule smaller than Absorica®. The smaller sized capsule would be advantageous for patients as it would be easier for swallowing.

SUMMARY OF THE INVENTION

The present invention provides a low dose oral pharmaceutical composition of isotretinoin having reduced food effect, in particular no food effect. The oral pharmaceutical composition of the present invention comprises isotretinoin and a pharmaceutically acceptable excipient. The present composition is in the form of a dispersion which is further filled into capsules. The present invention further provides a process for preparing the oral pharmaceutical composition of the present invention. It also provides a method of treating severe acne by administering the oral pharmaceutical composition of the present invention.

DETAILED DESCRIPTION OF THE INVENTION

In one aspect, the present invention provides a low dose oral pharmaceutical composition comprising isotretinoin and a pharmaceutically acceptable excipient.

In another aspect, the present invention provides a low dose oral pharmaceutical composition comprising isotretinoin and a pharmaceutically acceptable excipient, wherein said composition, when administered orally, provides an equivalent efficacy at a lower dose of isotretinoin in comparison to the marketed Absorica® capsules, wherein said dose is at least 10% lower.

In another aspect, the present invention provides a low dose oral pharmaceutical composition comprising isotretinoin and a pharmaceutically acceptable excipient, wherein said composition, when administered orally, provides an equivalent efficacy at a lower dose of isotretinoin in comparison to the marketed Absorica® capsules, wherein said dose is at least 20% lower.

In another aspect, the present invention provides a low dose oral pharmaceutical composition comprising isotretinoin and a pharmaceutically acceptable excipient, wherein said composition exhibits reduced food effect in particular no food effect as indicated by comparable $C_{max}$ in fasting and fed states.

In an embodiment of the above aspect, the composition exhibits a mean $C_{max}$ of about 451.38 ng/mL under fed condition and a mean $C_{max}$ of about 454.92 ng/mL under fasting condition.

In another embodiment of the above aspect, the composition exhibits a mean AUC of about 6514.86 ng·h/mL under fed condition and a mean AUC of about 5566.90 ng·h/mL under fasting condition.

In another embodiment of the above aspect, the composition, when administered orally, has a mean fed/fasted ratio of AUC of about 1.17 and a mean fed/fasted ratio of $C_{max}$ of about 0.99.

In another aspect, the present invention provides an oral pharmaceutical composition comprising isotretinoin and a pharmaceutically acceptable excipient, wherein the composition has a mean $C_{max}$ value in the range of about 9 ng/mL/mg to about 40 ng/mL/mg when administered in a dose of about 0.4 mg/kg to about 1.6 mg/kg of the body weight in a human subjects under fasting conditions.

In one embodiment of the above aspect, the composition further provides $AUC_{0-t}$ value in the range of about 125 ng·h/mL/mg to about 500 ng·h/mL/mg under fasting condition.

In another aspect, the present invention provides a pharmaceutical composition of isotretinoin and a pharmaceutically acceptable excipient wherein the composition exhibits no food effect and has a mean fed/fasted ratio of $C_{max}$ value of about 0.85 to about 1.22, when administered in a dose of about 0.4 mg/kg to about 1.6 mg/kg of the body weight in a human subjects.

The term "no food effect" as used herein means that formulation can be given with or without food. Further, there is no significant impact on $C_{max}$ value when given in fed or fasted state. The mean fed/fasted ratio of $C_{max}$ value are preferably in the range of about 0.85 to about 1.22.

In one embodiment of the above aspect, the composition has a mean fed/fasted ratio of $AUC_{0-t}$ value of about 0.9 to about 1.40.

In another aspect, the present invention provides a low dose oral pharmaceutical composition comprising:
  (a) isotretinoin; and
  (b) an oily vehicle.

In another embodiment of the above aspects, the composition comprises:
  (a) isotretinoin in an amount of about 5.0 w/w to about 15 w/w based on the total weight;
  (b) an oily vehicle, and (c) surfactant in amount of about 0.05% w/w to about 10% w/w based on the total weight.

In one embodiment of the above aspect, said composition comprises isotretinoin in an amount of about 1 mg to 100 mg, 5 mg to 50 mg, 10 mg to 40 mg, 9 mg to 36 mg, or 8 mg to 32 mg.

In another embodiment of the above aspect, said composition comprises isotretinoin in an amount of about 8 mg, 16 mg, 20 mg, 24 mg, 28 mg, or 32 mg.

In another embodiment of the above aspect, said composition comprises isotretinoin in an amount of about

| Lower dose isotretinoin composition (dose/capsule) | High dose marketed capsule comprising semi-solid suspension (dose/capsule) |
| --- | --- |
| about 6.5 mg to about 9.0 mg | 10 mg |
| about 13 mg to about 18 mg | 20 mg |
| about 16.25 mg to about 22.5 mg | 25 mg |
| about 19.5 mg to about 27 mg | 30 mg |
| about 22.75 mg to about 31.5 mg | 35 mg |
| about 26 mg to about 36 mg | 40 mg |

In another embodiment of the above aspect, said composition is in the form of a dispersion which is further filled into capsules.

In another embodiment of the above aspect, the oily vehicle includes, but is not limited to, groundnut oil, olive oil, soybean oil, kernel oil, almond oil, safflower oil, sunflower oil, palm oil, sesame oil, canola oil, corn oil, castor oil, coconut oil, cotton seed oil, grape seed oil, and mixtures thereof.

In another embodiment of the above aspect, the oily vehicle is present in an amount of about 1% w/w to about 99% w/w by the total weight of the composition; preferably in an amount of about 10% w/w to about 95% w/w by the total weight of the composition.

In another embodiment of the above aspect, the oily vehicle is present in an amount of about 71% w/w to about 95% w/w by the total weight of the composition.

In another embodiment of the above aspect, the ratio of isotretinoin to the oily vehicle ranges from about 1:99 to about 99:1.

In another embodiment of the above aspect, the composition further comprises a surfactant.

In another embodiment of the above aspect, the surfactant includes, but is not limited to, anionic, cationic, or non-ionic surfactants; sorbitan fatty acid esters; polysorbates prepared from lauric, palmitic, stearic, and oleic acids; mononylphenyl ethers of polyethylene glycols such as nanoxynols; polyoxyethylene monoesters such as polyoxyethylethylene monostearate, polyoxyethylene monolaurate, and polyoxyethylene monooleate; dioctyl sodium sulfosuccinate; sodium lauryl sulphate; lecithin; fatty acid esters of propylene glycol; fatty acid esters of glycerol; poloxamers; and mixtures thereof.

In another embodiment of the above aspect, the surfactant is present in an amount of about 0.05% w/w to about 10.0% w/w by the total weight of the composition.

In yet another embodiment of the above aspect, the composition further comprises other excipients like antioxidants, preservatives, and alkaline stabilizers.

In yet another embodiment of the above aspect, the composition is substantially free of wax.

The term "substantially free of wax" as used herein means that the composition contains wax less than about 10% by weight of the composition, in particular less than 8% by weight.

In yet another embodiment of the above aspect, the composition is free of wax.

In yet another embodiment of the above aspect, the composition comprises isotretinoin wherein the particle size distribution of isotretinoin is such that the $D_{90}$ is less than 60 µm, less than 55 µm, less than 50 µm, less than 45 µm, less than 40 µm, less than 35 µm, less than 30 µm, less than 25 µm, less than 20 µm, less than 15 µm, or less than 10 µm.

In yet another embodiment of the above aspect, the composition comprises isotretinoin wherein the particle size distribution of isotretinoin is such that the $D_{90}$ is less than 30 µm.

In another embodiment of the above aspect, the composition comprises isotretinoin wherein the particle size distribution of isotretinoin is such that the $D_{50}$ is less than 40 µm, less than 35 µm, less than 30 µm, less than 25 µm, less than 20 µm, less than 15 µm, less than 10 µm, or less than 5 µm.

In yet another embodiment of the above aspect, the composition comprises isotretinoin wherein the particle size distribution of isotretinoin is such that the $D_{50}$ is less than 15 µm.

In another embodiment of the above aspect, the composition comprises isotretinoin wherein the particle size distribution of isotretinoin is such that the $D_{10}$ is less than 20 µm, less than 18 µm, less than 17 µm, less than 15 µm, less than 12 µm, less than 10 µm, less than 8 µm, less than 7 µm, less than 5 µm, or less than 2 µm.

In yet another embodiment of the above aspect, the composition comprises isotretinoin wherein the particle size distribution of isotretinoin is such that the $D_{10}$ is less than 7 µm.

In yet another embodiment of the above aspect, the composition comprises isotretinoin wherein the particle size distribution of isotretinoin is such that the $D_{90}$ is less than 60 µm and the $D_{50}$ is less than 40 µm.

In yet another embodiment of the above aspect, the composition comprises isotretinoin wherein the particle size distribution of isotretinoin is such that the $D_{90}$ is less than 60 µm, $D_{50}$ is less than 40 µm, and $D_{10}$ is less than 20 µm.

In yet another embodiment of the above aspect, the composition comprises isotretinoin wherein the particle size distribution of isotretinoin is such that the $D_{90}$ is less than 30 µm, $D_{50}$ is less than 15 µm, and $D_{10}$ is less than 10 µm.

In yet another embodiment of the above aspect, the composition comprises isotretinoin wherein the particle size distribution of isotretinoin is such that the ratio of $D_{90}/D_{50}$ is about 1.5-2.5 µm, $D_{50}/D_{10}$ is about 1.8 to 3.3 and $D_{90}/D_{10}$ is about 3.0 to 6.1.

In another aspect, the present invention provides a stable oral pharmaceutical composition comprising isotretinoin and a pharmaceutically acceptable excipient wherein the composition contains not more than 1% w/w 5, 6-epoxy-13-cis retinoic acid when stored at a temperature 40° C. and 75% relative humidity for a period of six months.

In one embodiment of the above aspect, the composition is filled in a capsule having a fill occupancy more than 40%.

In another embodiment of the above aspect, the composition in the form of dispersion is filled in hard gelatin capsule.

In another aspect, the present invention provides a stable oral pharmaceutical composition comprising isotretinoin and a pharmaceutically acceptable excipient wherein said composition is filled in a following capsule size:

| Dose/Capsule | Capsule size |
| --- | --- |
| 8 mg | Size 2 or smaller |
| 16 mg | Size 1 or smaller |
| 20 mg | Size 0 or smaller |
| 24 mg | Size 0 or smaller |
| 28 mg | Size 00 or smaller |
| 32 mg | Size 00 or smaller |

In one embodiment of the above aspect, the composition has isotretinoin to excipient ratio 1:5 to 1:18.

In another embodiment of the above aspect, the composition has fill weight of less than 600 mg (excluding capsule shell weight).

In another aspect, there is provided a process for the preparation of a low dose oral pharmaceutical composition comprising isotretinoin and an oily vehicle wherein the process comprises:

(a) dispersing isotretinoin in an oily carrier;

(b) milling the dispersion to get the desired particle size;

(c) adding one or more excipients to the above dispersion;

(d) optionally adding an oily carrier to the dispersion of step (c); and (e) filling the dispersion into capsules.

In another aspect, there is provided a process for the preparation of a low dose oral pharmaceutical composition comprising isotretinoin and an oily vehicle wherein the process comprises:

(f) dispersing isotretinoin in an oily carrier;

(g) milling the dispersion to get the desired particle size;

(h) adding one or more excipients to the above dispersion;

(i) adding an oily carrier to the dispersion of step (c); and (j) filling the dispersion into capsules.

In one embodiment of the above aspect, the oily carrier used in step (a) is present in an amount which is at least 25% w/w of the total amount of the oily carrier.

In another embodiment of the above aspect, the composition has a density of 0.8 to 1.1 g/mL.

In still another aspect, the present invention provides a method of treating severe acne, musculoskeletal and connective tissue inflammations, emphysema, ulcerating diseases, cervical tumors in HIV positive women, lung cancer in smokers, skin cancer, neuroblastoma, recurrent prostate cancer, leukemia, high-grade glioma, head and neck cancers, multiple myeloma, gram-negative folliculitis, recalcitrant rosacea, pyoderma faciale, psoriasis, cutaneous lupus erythematosus, acne fulminans, squamous cell carcinoma, or cutaneous photoaging by administering to the individual in need thereof, a low dose oral pharmaceutical composition of the present invention.

In one embodiment of the above aspect, the present invention provides a method of treating acne by administering to the individual in need thereof, a low dose oral pharmaceutical composition of the present invention.

In another aspect, the present invention provides a method of treating severe recalcitrant nodular acne in a patient in need thereof wherein said method comprises administering isotretinoin in an amount of about 0.4 to about 1.6 mg per kilogram of the body weight; wherein the body weight of the patient and the selected dose correlate to one of the following:

| Body Weight | | Total Daily (mg) | | |
| --- | --- | --- | --- | --- |
| Kg | Pounds | 0.4 mg/kg | 0.8 mg/kg | 1.6 mg/kg |
| 40 | 88 | 16 | 32 | 64 |
| 50 | 110 | 20 | 40 | 80 |
| 60 | 132 | 24 | 48 | 96 |
| 70 | 154 | 28 | 56 | 112 |
| 80 | 176 | 32 | 64 | 128 |
| 90 | 198 | 36 | 72 | 144 |
| 100 | 220 | 40 | 80 | 160 |

In one embodiment of the above aspect, the dose is given twice daily for 15-20 weeks.

In another aspect, the present invention provides an oral pharmaceutical composition comprising isotretinoin and a pharmaceutically acceptable excipient, wherein said composition has an isotretinoin to excipient ratio of about 1:5 to about 1:18 and releases not less than 50% of isotretinoin in 15 minutes when measured in United States Pharmacopeia (USP) type II dissolution apparatus, paddle at 75 rpm, in 900 mL of pH 7.4 phosphate buffer with 70 mg/L Pancreatin and 4.5% lauryldimethylamine oxide (as 30% solution) with spiral coated sinker.

In one embodiment of the above aspect, the composition releases not less than 85% in 30 minutes.

In another embodiment of the above aspect, the composition has viscosity of about 50 to 450 cps at room temperature. The viscosity was measured by Brookfield Viscometer, spindle number S-02 stirred at 20 RPM.

In another aspect, the present invention provides an oral pharmaceutical composition comprising isotretinoin and a pharmaceutically acceptable excipient, wherein said composition releases not less than 50% of isotretinoin in 15 minutes when measured in United States Pharmacopeia (USP) type II dissolution apparatus, paddle at 75 rpm, in 900 mL of borate Buffer (pH 8.0) containing 0.5% cetrimide and 50 mg/L of pancreatin (with alternate sinkers).

The term "isotretinoin" refers to isotretinoin in its crystalline or amorphous form, as well as its esters, salts, or derivatives thereof. Isotretinoin is present in an amount of about 5.5% to about 15% based on the total weight of the composition The term "low dose," as used herein, refers to the dose of isotretinoin wherein said dose is at least about 10% lower than the presently approved dose.

The bioequivalence is established by comparing pharmacokinetic parameters, for example, AUC and $C_{max}$ of the pharmaceutical composition of the present invention with Absorica® formulation in healthy human subjects in fed as well as fasting conditions.

The term "AUC" refers to the area under the time/plasma concentration curve after administration of the pharmaceutical composition. $AUC_{0-\infty}$ denotes the area under the plasma concentration versus time curve from time 0 to infinity; $AUC_{0-t}$ denotes the area under the plasma concentration versus time curve from time 0 to time t.

The term "$C_{max}$" refers to the maximum concentration of isotretinoin in the blood following administration of the pharmaceutical composition.

The term "$t_{max}$" refers to the time in hours when $C_{max}$ is achieved following administration of the pharmaceutical composition.

The term "$D_{10}$" refers to the particle size of isotretinoin where 10% (w/v) of the particles have a size less than the defined $D_{10}$ value; "$D_{50}$" refers to the particle size of isotretinoin where 50% (w/v) of the particles have a size less than the defined $D_{50}$ value; "$D_{90}$" refers to the particle size of isotretinoin where 90% (w/v) of the particles have a size less than the defined $D_{90}$ value, when measured through Malvern Instrument Ltd.

"Defined $D_{10}$ value/$D_{50}$ value/$D_{90}$ value" refers to the values defined in the embodiments.

Examples of suitable antioxidants include, but are not limited to, butylated hydroxyl anisole, butylated hydroxyl toluene, tocopherol, ascorbyl palmitate, ascorbic acid, sodium metabisulfite, sodium sulfite, sodium thiosulfate, propyl gallate, and mixtures thereof. The antioxidant is present in an amount of about 0.002% w/w to about 2% w/w of the total composition.

Examples of alkaline stabilizers include, but are not limited to, sodium hydroxide, potassium hydroxide, sodium carbonate or bicarbonate, potassium carbonate or bicarbonate, lithium hydroxide, triethylamine, meglumine, methylamine, and mixtures thereof.

Examples of suitable preservatives include, but are not limited to, methyl paraben, ethyl paraben, propyl paraben, butyl paraben, benzoic acid, sodium benzoate, benzyl alcohol, sorbic acid, potassium sorbate, and mixtures thereof.

The term "stable," as used herein, refers to chemical stability, wherein not more than 1.5% w/w of total related substances (excluding tretinoin) are formed on storage at accelerated conditions of stability at 40° C. and 75% relative humidity or at 25° C. and 60% relative humidity for a period of at least six months or to the extent necessary for use of the composition. Further, composition contains not more than 1% w/w 5, 6-epoxy-13-cis retinoic acid when stored at a temperature 40° C. and 75% relative humidity for a period of six months.

The size reduction of isotretinoin is achieved by wet milling the dispersion of isotretinoin in an oily vehicle using mechanical means such as a jet mill, ball mill, or media mills such as a sand mill, DYNO®-mill, or a bead mill. The grinding media in these mills can comprise spherical particles such as stainless steel beads or zirconium oxide balls.

The term "about", as used herein, refers to any value which lies within the range defined by a variation of up to ±10% of the value.

The invention may be further illustrated by the following examples, which are for illustrative purposes only and should not be construed as limiting the scope of the invention in any way.

EXAMPLES

Example 1

| S. No. | Ingredients | Quantity (% w/w) |
|---|---|---|
| 1 | Isotretinoin | 6.67 |
| 2 | Butylated hydroxy anisole | 0.04 |
| 3 | Polysorbate 80 | 1.85 |
| 4 | Soybean oil | 91.44 |

Procedure:
1. Butylated hydroxy anisole and polysorbate 80 were dissolved in soybean oil (39.36% w/v of the total composition) to form a clear solution.
2. Isotretinoin was added to the step 1 solution under stirring to obtain a uniform dispersion.
3. The dispersion of step 2 was milled to get the particle size of isotretinoin such that $D_{90}$ was about 20 μm.
4. The remaining quantity of soybean oil (52.08% w/v of the total composition) was added to the micronized dispersion of step 3 under stirring to obtain a uniform dispersion.
5. The dispersion of step 4 was filled into hard gelatin capsules.

Dissolution Studies

The pharmaceutical composition of Example 1 (containing 16 mg of isotretinoin) was compared with the marketed formulation of isotretinoin (20 mg Absorica® capsules) for the release profile in an FDA recommended dissolution medium as given in the following tables:

Reference (R): Absorica® 20 mg capsules
Test (T): Isotretinoin 16 mg capsules (Example 1)

| Dissolution Media | pH 7.8 phosphate buffer with 0.5% w/v N,N-dimethyl dodecylamine N-oxide |
|---|---|
| Apparatus/RPM/Vol | USP Type I (20 mesh basket)/100/900 mL |

| | % of Drug Released Over Time (minutes) | | | | | | | | |
|---|---|---|---|---|---|---|---|---|---|
| Sample | 10 | 15 | 20 | 30 | 45 | 60 | 90 | 120 | 150 |
| Test | 34 | — | 58 | 73 | 93 | 99 | 100 | 101 | 100 |
| Reference | 0 | — | 2 | 6 | 24 | 37 | 58 | 76 | 83 |

Pharmacokinetic Study Under Fed Conditions

The pharmaceutical composition of Example 1 (containing 16 mg of isotretinoin) was compared with the marketed formulation of isotretinoin (20 mg Absorica® capsules) under fed conditions on 15 healthy adult male subjects.

Values for various pharmacokinetic parameters, including observed $C_{max}$, $AUC_{0-t}$, and $AUC_{0-inf}$ were calculated and are provided in Table 1 below.

Reference (R): Absorica® 20 mg capsules
Test (T): Isotretinoin 16 mg capsules (Example 1)

TABLE 1

Comparative pharmacokinetic data for test and reference in 15 healthy adult human male subjects

| | In $C_{max}$ | In $AUC_{0-t}$ | In $AUC_{0-inf}$ |
|---|---|---|---|
| Ratio (T/R) | 111.07 | 90.12 | 91.59 |
| 90% CI | 91.54-134.76 | 84.30-96.35 | 86.32-97.19 |

Average $t_{max}$ values for both the test and reference are 4.7888 hours and 5.5111 hours, respectively, which indicate a comparable absorption pattern.

Under fed conditions, the test prototype shows a comparable extent of absorption to reference product with T/R ratios of 90.12% and 91.59% for $AUC_{0-t}$ and $AUC_{0-inf}$, respectively. These values are within the regulatory acceptance criteria of 80% to 125%. However, for rate of absorption ($C_{max}$), the ratio is observed to be slightly on a higher side (111.07%) with 90% CI ranging between 91.54% and 134.76%.

Pharmacokinetic Study Comparing the Formulation of Example 1 Under Fed and Fasting Conditions The pharmaceutical composition of Example 1 (16 mg Test capsule) was compared in fed and fasting conditions on 15 healthy adult male subjects.

Values for various pharmacokinetic parameters, including observed $C_{max}$, $AUC_{0-t}$, and $AUC_{0-inf}$ were calculated and are provided in Table 2 below.

Test (A): Isotretinoin 16 mg capsules (Example 1) under fasting conditions
Test (B): Isotretinoin 16 mg capsules (Example 1) under fed conditions

TABLE 2

Comparative pharmacokinetic data for test (B) vs test (A) in 15 healthy adult human male subjects:

|  | In $C_{max}$ | In $AUC_{0-t}$ | In $AUC_{0\text{-}inf}$ |
|---|---|---|---|
| Ratio (B/A) | 99.22 | 116.34 | 117.02 |
| 90% CI | 81.78-120.38 | 108.82-124.37 | 110.29-124.17 |

Average $t_{max}$ for the test prototype under fasting condition (3.7667 hours) is ~1.02 hours earlier than when administered under fed condition (4.7888 hours).

On comparing the test prototype under fasting and fed conditions, it is observed that B/A ratio for rate of absorption ($C_{max}$) is close to unity (99.22%). Even though B/A ratios are on higher side for the AUC values, (approx. 116% to 117%), the 90% CI for all three PK parameters ($C_{max}$, $AUC_{0-t}$, and $AUC_{0\text{-}inf}$) are within the 80% to 125% regulatory acceptance criteria.

Conclusion:
The 16 mg test prototype has comparable bioavailability to the reference product (Absorica® 20 mg) under fed conditions. This provides positive support for up to 20% reduction in the test dose.

There is no indication that food will significantly impact the rate and extent of drug absorption from the test prototype. In fact, we observe that T/R ratios and 90% CI for the PK parameters are within the 80% to 125% regulatory acceptance criteria.

Example 2

| S. No | Name of Ingredient | Quantity (% w/w) |
|---|---|---|
| 1. | Isotretinoin | 13.91 |
| 2. | Polysorbate 80 | 3.86 |
| 3. | Butylated hydroxy anisole | 0.08 |
| 4. | Soybean Oil | 82.15 |

Procedure:
1. Butylated hydroxy anisole and polysorbate 80 were dissolved in the soybean oil to form a clear solution.
2. Isotretinoin was added to the step 1 solution under stirring to obtain a uniform dispersion.
3. The dispersion of step 2 was milled to get the particle size of isotretinoin such that $D_{90}$ was about 20 μm.
4. The dispersion of step 3 was filled into hard gelatin capsules.
5. The filled capsules of step 4 were sealed using a gelatin solution.

Example 3

| S. No | Name of Ingredient | Quantity (% w/w) |
|---|---|---|
| 1. | Isotretinoin | 6.67 |
| 2. | Butylated Hydroxy Anisole | 0.04 |
| 3. | Soybean Oil | 93.29 |

Procedure:
1. Butylated hydroxy anisole was dissolved in soybean oil (39.36% w/v of the total composition) to form a clear solution.
2. Isotretinoin was added to the step 1 solution under stirring to obtain a uniform dispersion.
3. The dispersion of step 2 was milled to get the particle size of isotretinoin such that $D_{90}$ was about 20 μm.
4. The remaining quantity of soybean oil (53.93% w/v of the total composition) was added to the micronized dispersion of step 3 under stirring to obtain a uniform dispersion.
5. The dispersion of step 4 was filled into hard gelatin capsules.
6. The filled capsules of step 5 were sealed using a gelatin solution.

Dissolution Studies (USP Test-4)

The pharmaceutical composition according to Example 1 (containing 24 mg of isotretinoin) was compared with the marketed formulation of high dose isotretinoin (30 mg Absorica® capsules) for the release profile in a USP Test-4 as given in the following Table 3:

Reference (R): Absorica® 30 mg capsules
Test (T): Isotretinoin 24 mg capsules (Example 1)

TABLE 3

Percent drug release in USP Test-4

| Dissolution Media (USP Test-4) | Phosphate Buffer (pH 7.4) containing with 70 mg/L Pancreatin and 4.5% LDAO as 30% solution |
| Apparatus/RPM/Vol | USP Type II (with coated spiral sinkers)/75/900 mL |

% of Drug Released Over Time (minutes)

| | Sample Time | | | | |
|---|---|---|---|---|---|
| | 15 | 30 | 45 | 60 | 90 |
| Test | 80 | 97 | 97 | 96 | 95 |
| Reference | 6 | 29 | 54 | 74 | 89 |

Dissolution Studies (USP Test-3)

The pharmaceutical composition of Example 1 (containing 32 mg of isotretinoin) was compared with the marketed formulation of isotretinoin (40 mg Absorica® capsules) for the release profile in a USP Test-3 as given in the following Table 4:

Reference (R): Absorica® 40 mg capsules
Test (T): Isotretinoin 32 mg capsules (Example 1)

TABLE 4

Percent drug release in USP Test-3

| Dissolution Media (USP Test-3) | Borate Buffer (pH 8.0) containing 0.5% cetrimide and 50 mg/L of pancreatin |
| Apparatus/RPM/Vol | USP Type II (with alternative sinkers)/75/900 mL |

% of Drug Released Over Time (minutes)

| | Sample Time | | | | |
|---|---|---|---|---|---|
| | 15 | 30 | 45 | 60 | 90 |
| Reference | 3 | 21 | 48 | 67 | 84 |
| Test | 64 | 86 | 91 | 93 | 96 |

Pharmacokinetic Study Comparing the Formulation of Example 1 Under Fed and Fasting Conditions The pharmaceutical composition according to Example 1 (32 mg Test capsule) was compared in fed and fasting conditions on 72 healthy adult male and female subjects. The study has been conducted as an open-label, multiple-(clinical) centre, balanced randomized, single-dose, three-treatment, three-period, six-sequence, crossover study.

Values for various pharmacokinetic parameters, including observed $C_{max}$, $AUC_{0-t}$, and $AUC_{0-inf}$ were calculated and are provided in Table 5 below.

Test (A): Isotretinoin 32 mg capsules (Example 1) under fasting conditions
Test (B): Isotretinoin 32 mg capsules (Example 1) under fed conditions

TABLE 5

Comparative pharmacokinetic data for test (B) vs test (A) in 72 healthy adult human subjects: Study 1

|  | Mean $C_{max}$ | Mean $AUC_{0-t}$ | Mean $AUC_{0-\infty}$ |
|---|---|---|---|
| Fasted Condition (A) | 539.4 | 8042 | 8711 |
| Fed condition (B) | 583.9 | 10039 | 10736 |
| Ratio (B/A) | 1.08 | 1.24 | 1.23 |
| 90% CI | 94.42-124.12 | 117.29-132.88 | 115.93-131.01 |
| Per mg values | 16.84 | 251.31 | 272.22 |

Conclusion:

The results summarized in Table 5 demonstrates that there is no effect on $C_{max}$ and only marginal increase of AUC. Hence, food does not affect bioavailability of test formulation of Example 1.

Stability Data:

Table 6 provides the impurity profile of Example 1 (16 mg) when stored at a temperature of 40° C. and 75% relative humidity for the period of six months. Impurities were determined using HPLC system.

TABLE 6

Stability data of isotretinoin when stored at a temperature of 40° C. and 75% relative humidity for the period of six months.

| Impurities | 6 months/40° C./75% RH |
|---|---|
| 5,6-epoxy-13-cis retinoic acid | 0.28 |
| Total impurities | 1.24 |

Example 4

| S. No. | Ingredients | Qty/capsule (mg) | |
|---|---|---|---|
| 1 | Isotretinoin | 8 | 16 |
| 2 | Butylated hydroxy anisole | 0.045 | 0.090 |
| 3 | Polysorbate 80 | 2.220 | 4.440 |
| 4 | Soybean oil | 109.735 | 219.470 |
|  | Total weight | 120.00 | 240.00 |

Procedure:

1. Butylated hydroxy anisole and polysorbate 80 were dissolved in soybean oil (39.36% w/v of the total composition) to form a clear solution.
2. Isotretinoin was added to the step 1 solution under stirring to obtain a uniform dispersion.
3. The dispersion of step 2 was milled to get the particle size of isotretinoin such that $D_{90}$ was about 20 μm.
4. The remaining quantity of soybean oil (52.08% w/v of the total composition) was added to the micronized dispersion of step 3 under stirring to obtain a uniform dispersion.
5. The dispersion of step 4 was filled into hard gelatin capsules.

TABLE 7

Composition parameters of Example 4

| Composition parameters | 16 mg |
|---|---|
| Density | 0.95 g/mL |
| Fill Occupancy | 68.38% |
| Viscosity | 264 Centipoise (at room temperature) |

The invention claimed is:

1. An oral pharmaceutical composition in the form of a capsule comprising isotretinoin and a pharmaceutically acceptable excipient, wherein the composition has a mean $C_{max}$ value in the range of about 9 ng/mL/mg to about 40 ng/mL/mg when administered in a dose of about 0.4 mg/kg to about 1.6 mg/kg of the body weight in a human subjects under fasting conditions.

2. The oral pharmaceutical composition in the form of a capsule of isotretinoin according to claim 1 wherein the composition has $AUC_{0-t}$ in the range of about 125 ng·h/mL/mg to about 500 ng·h/mL/mg under fasting condition.

3. The oral pharmaceutical composition in the form of a capsule of isotretinoin according to claim 2 wherein composition exhibits mean fed/fasted ratio of $AUC_{0-t}$ value of about 0.9 to about 1.40.

4. The oral pharmaceutical composition in the form of a capsule composition according to claim 1 wherein the composition is in the form of a dispersion which is further filled into the capsules.

5. The oral pharmaceutical composition in the form of a capsule composition according to claim 1 wherein the isotretinoin is micronized and has $D_{90}$ less than 30 μm.

6. The oral pharmaceutical composition in the form of a capsule composition according to claim 1 wherein the isotretinoin is present in an amount of about 5.5% to about 15% based on the total weight of the composition.

7. The oral pharmaceutical composition in the form of a capsule composition according to claim 1 wherein the composition further comprises a surfactant.

8. The oral pharmaceutical composition in the form of a capsule composition according to claim 7 wherein the surfactant is selected from the group consisting of anionic, cationic or non-ionic surfactants, sorbitan fatty acid esters; polysorbates; mononylphenyl ethers of polyethyleneglycols; dioctyl sodium sulfosuccinate, sodium lauryl sulphate, lecithin, fatty acid esters of propylene glycol, fatty acid esters of glycerol, poloxamers, and mixtures thereof.

9. The oral pharmaceutical composition in the form of a capsule according to claim 1, wherein the composition releases not less than 50% of isotretinoin in 15 minutes when measured in United States Pharmacopeia (USP) type II dissolution apparatus, paddle at 75 rpm, in 900 mL of pH 7.4 phosphate buffer with 70 mg/L pancreatin and 4.5% LDAO as 30% solution with spiral coated sinker.

\* \* \* \* \*